United States Patent
Cosman et al.

(10) Patent No.: US 6,978,815 B2
(45) Date of Patent: Dec. 27, 2005

(54) SYSTEM AND METHOD FOR FORMING BIOENGINEERED TUBULAR GRAFT PROSTHESES

(75) Inventors: Maury D. Cosman, Medfield, MA (US); Kristen Billiar, Jamaica Plain, MA (US); Ryan Mercer, Richmond, CA (US); Bruce Miller, North Quincy, MA (US)

(73) Assignee: Organogenesis Inc., Canton, MA (US)

( * ) Notice: Subject to any disclaimer, the term of this patent is extended or adjusted under 35 U.S.C. 154(b) by 220 days.

(21) Appl. No.: 10/325,444

(22) Filed: Dec. 19, 2002

(65) Prior Publication Data

US 2003/0234469 A1 Dec. 25, 2003

(Under 37 CFR 1.47)

Related U.S. Application Data

(60) Provisional application No. 60/342,831, filed on Dec. 21, 2001.

(51) Int. Cl.$^7$ .............................................. B65H 81/00
(52) U.S. Cl. ...................................... 156/447; 156/446
(58) Field of Search ................................ 156/425, 429, 156/443, 446, 447, 457

(56) References Cited

U.S. PATENT DOCUMENTS

| | | | |
|---|---|---|---|
| 3,345,934 A | 10/1967 | Steiner et al. | |
| 5,993,844 A | 11/1999 | Abraham et al. | |
| 6,089,409 A | 7/2000 | Hart et al. | |
| 6,187,039 B1 * | 2/2001 | Hiles et al. | 623/1.44 |
| 6,358,284 B1 * | 3/2002 | Fearnot et al. | 623/23.72 |
| 2002/0083840 A1 | 7/2002 | Lassota | |

FOREIGN PATENT DOCUMENTS

| | | |
|---|---|---|
| WO | WO 95/22301 | 8/1995 |
| WO | WO 99/62424 | 12/1999 |
| WO | WO 99/62425 | 12/1999 |
| WO | WO 99/62427 | 12/1999 |

OTHER PUBLICATIONS

Staros, "N–Hydroxysulfosuccinimide Active Esters: Bis (N–hydroxysulfosuccinimide) Esters of Two Dicarboxylic Acids Are Hydrophilic, Membrane–Impermeant, Protein Cross–Linkers," Biochemistry, 1982, 21: 3950–3955.

* cited by examiner

*Primary Examiner*—Jeff H. Aftergut
(74) *Attorney, Agent, or Firm*—Wilmer Cutler Pickering Hale and Dorr LLP

(57) ABSTRACT

An apparatus for forming a tube construct from a planar sheet matrix includes a stand supporting two opposing mounts and spanning between the opposing mounts are a mandrel, a porous rod, and a spring-loaded roller held in parallel arrangement; a guide for aligning and engaging the mandrel on the opposing mounts; and a means for imparting a tangential force on the planar sheet matrix to prevent wrinkling. The porous rod has a lumen running its length and has pores that communicate between the lumen of the porous rod through to the surface of the rod for water to uniformly pass through. The spring-loaded roller runs along the length of the porous rod creating a line of contact between the roller and the mandrel. The mandrel is contacted with a planar sheet of matrix and is rotated such that successive portions of the matrix contact the porous rod and become lightly moistened by the water passing through the pores of the porous rod and become wrapped around the mandrel to form a tube construct.

8 Claims, 3 Drawing Sheets

SYSTEM AND METHOD FOR FORMING BIOENGINEERED TUBULAR GRAFT PROSTHESES

CROSS-REFERENCE TO RELATED APPLICATION

This application claims the benefit of U.S. Provisional Application Ser. No. 60/342,831 entitled "SYSTEM AND METHOD FOR FORMIING BIOENGINEERED TUBULAR GRAFT PROSTHESES" filed on Dec. 21, 2001, which is incorporated herein by reference in its entirety.

FIELD OF THE INVENTION

This invention is in the field of tissue engineering. The invention is directed to a system and a method for preparing bioengineered graft prostheses prepared from cleaned tissue material derived from animal sources. The bioengineered graft prostheses made using the invention are tubular, of small diameter, and have a uniform geometry along their entire length. The bioengineered graft prostheses are used for implantation, repair, or for use in a mammalian host.

BACKGROUND OF THE INVENTION

The present invention overcomes the difficulties in forming a fine gauge tube of uniform geometry from processed tissue matrix or reconstituted matrix.

SUMMARY OF THE INVENTION

The invention is a system for fabricating tubular constructs from planar sheet-like processed tissue matrices or reconstituted matrices. The system comprises two devices: a flagging device and a rolling device. Each device accommodates a mandrel on which the tubular construct is formed. First, a matrix is flagged on the mandrel using the flagging device. Second, the matrix is then rolled onto the mandrel using the rolling device.

Therefore, the method of the invention comprises: (a) a method for flagging a sheet of processed tissue matrix by aligning a mandrel along one edge of the sheet and contacting it to the sheet so that the sheet and the matrix adhere, and (b) rolling the flagged sheet around the mandrel while maintaining even tension on the sheet and smoothing out bubbles or creases as it is rolled onto the mandrel. Rolling continues until the sheet contacts and overlaps itself to a degree. The overlap is the bonding region that keeps the tissue in a tubular form.

DETAILED DESCRIPTION

Figure 1:
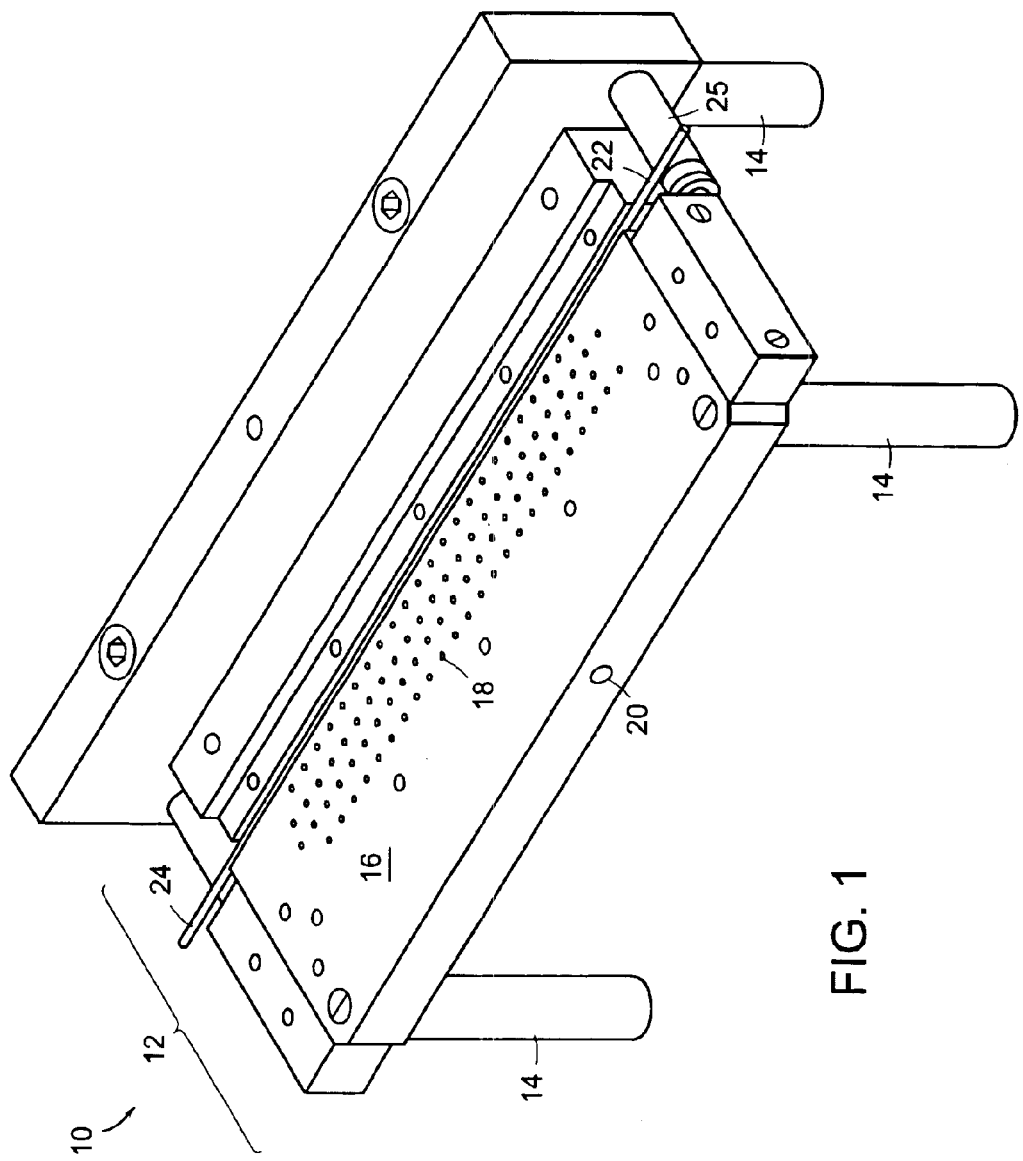
FIG. 1 shows a view of the flagging apparatus of the invention.

The invention is directed toward a system and methods for making tubular-shaped tissue engineered prostheses from thin planar materials where the system and methods do not require adhesives, sutures, or staples to bond the tissue in a tubular form and consequently maintain the bioremodelability of the prostheses.

Advantages provided by the invention are that the apparatus can make constructs faster and more consistently than if made manually. The system devices of the invention aid in even circumferential tensioning and radial compression of the tissue which smoothes out air or water bubbles or creases that can occur under the mandrel or between the layers of the tube. Because the constructs are used as medical devices, minimal variations can potentially affect the functional performance of the constructs when implanted in a patient.

The terms "processed tissue matrix" and "processed tissue material" mean native, normally cellular tissue that has been procured from an animal source, preferably a mammal, and mechanically cleaned of attendant tissues and chemically cleaned of cells, cellular debris, and rendered substantially free of non-collagenous extracellular matrix components. The processed tissue matrix, while substantially free cellular debris, maintains much of its native matrix structure, strength, and shape. Preferred compositions for preparing the bioengineered grafts of the invention are animal tissues comprising collagen, including, but not limited to: intestine, fascia lata, pericardium, dura mater, and other flat or planar structured tissues that comprise a fibrous tissue matrix. The planar structure of these tissue matrices makes them able to be easily manipulated and assembled using the devices and methods of the invention. A more preferred composition for preparing the bioengineered grafts of the invention is an intestinal collagen layer derived from the tunica submucosa of small intestine. Suitable sources for small intestine are mammalian organisms such as human, cow, pig, sheep, dog, goat, or horse while small intestine of pig is the preferred source. The most preferred composition for preparing tubular prostheses using the invention is a processed intestinal collagen layer derived from the tunica submucosa of porcine small intestine. To obtain the processed intestinal collagen layer, the small intestine of a pig is harvested and attendant mesenteric tissues are grossly dissected from the intestine. The tunica submucosa is preferably separated, or delaminated, from the other layers of the small intestine by mechanically squeezing the raw intestinal material between opposing rollers to remove the muscular layers (tunica muscularis) and the mucosa (tunica mucosa). The tunica submucosa of the small intestine is tougher than the surrounding tissue, hence the rollers squeeze the more friable components from the submucosa. In the examples that follow, the tunica submucosa was mechanically harvested from porcine small intestine using a Bitterling gut cleaning machine and then chemically cleaned to yield a cleaned tissue matrix as described in U.S. Pat. No. 5,993,844, the disclosure of which is incorporated herein by reference. This mechanically and chemically cleaned intestinal collagen layer is herein referred to as "ICL". ICL is used to prepare tubular constructs that are used as bioengineered medical devices such as those described in International PCT Application Publication Nos. WO 95/22301, WO 99/62424, WO 99/62425, and WO 99/62427, the teachings of which are incorporated herein by reference.

The terms, "reconstituted matrix" and "reconstituted material", mean animal-derived or cell-derived matrix components that have been extracted and purified from either tissues or cell cultures. The matrix may be formed from solubilized matrix components, principally collagen such that the matrix has tissue-like properties with regard to structure and physical properties. The reconstituted matrix may be highly purified and may have other components added to the matrix when the matrix is reformed. Other suitable collagenous tissue sources or other native tissue, reconstituted matrix sheets, or synthetic materials with the same flat sheet structure may be identified by the skilled artisan in other animal sources.

In the description of the devices and methods of the invention, and in the examples that follow, a sheet-like material, preferably either a processed tissue matrix or a reconstituted matrix, is used to make the tubular constructs. While not intending to be so limited but for simplicity in illustration of the apparatus and methods of the invention, and to describe the most preferred embodiment, the fabrication of a tube from a sheet of ICL will be described.

In the first aspect of the system of the invention, a flagging device is employed. Flagging introduces the ICL to be tubulated to a mandrel on which the tubular construct is formed. Referring to FIG. 1, shown is the flagging device of the invention. The flagging device 10 comprises a base platform 12 with legs 14. The platform incorporates a hollow chuck 16 with a plurality of machined holes 18 on its top facing surface, that communicate between the inside and outside of the chuck, and a port 20. The port 20 is connected to a vacuum source. Running along the surface of the platform 12 and along one edge of the hollow chuck 16 is a groove 22. The groove 22 accommodates a cylindrical mandrel 24 that is covered with an elastic sleeve and supported at each end by mandrel holders 25. The starting material, either a processed tissue matrix, such as ICL, or a reconstituted matrix, has a sheet-like geometry, preferably with at least one straight edge, more preferably rectangular. The ICL is dried in air before use. The sleeve on the mandrel is wetted with sterile water. The ICL is placed on the top surface of the platform with one edge of the material aligned along the center of the mandrel. The vacuum source is turned on to pull air through the machined holes 18 in the top of the hollow chuck 16. Because the vacuum is on, the ICL is held flat and even against the platform. The material is then contacted to the sleeve on the mandrel by raising the mandrel holders 25 so that only one edge of the ICL is contacted to the mandrel and is moistened by the water on the sleeve. The ICL, sticky when moistened, adheres to the mandrel. The ICL is allowed to dry to a point where it will remain adhered to the mandrel when the mandrel is lifted from the groove in the platform. A rectangular piece of ICL, when adhered to the mandrel along one edge, will resemble a flag.

Figure 2:
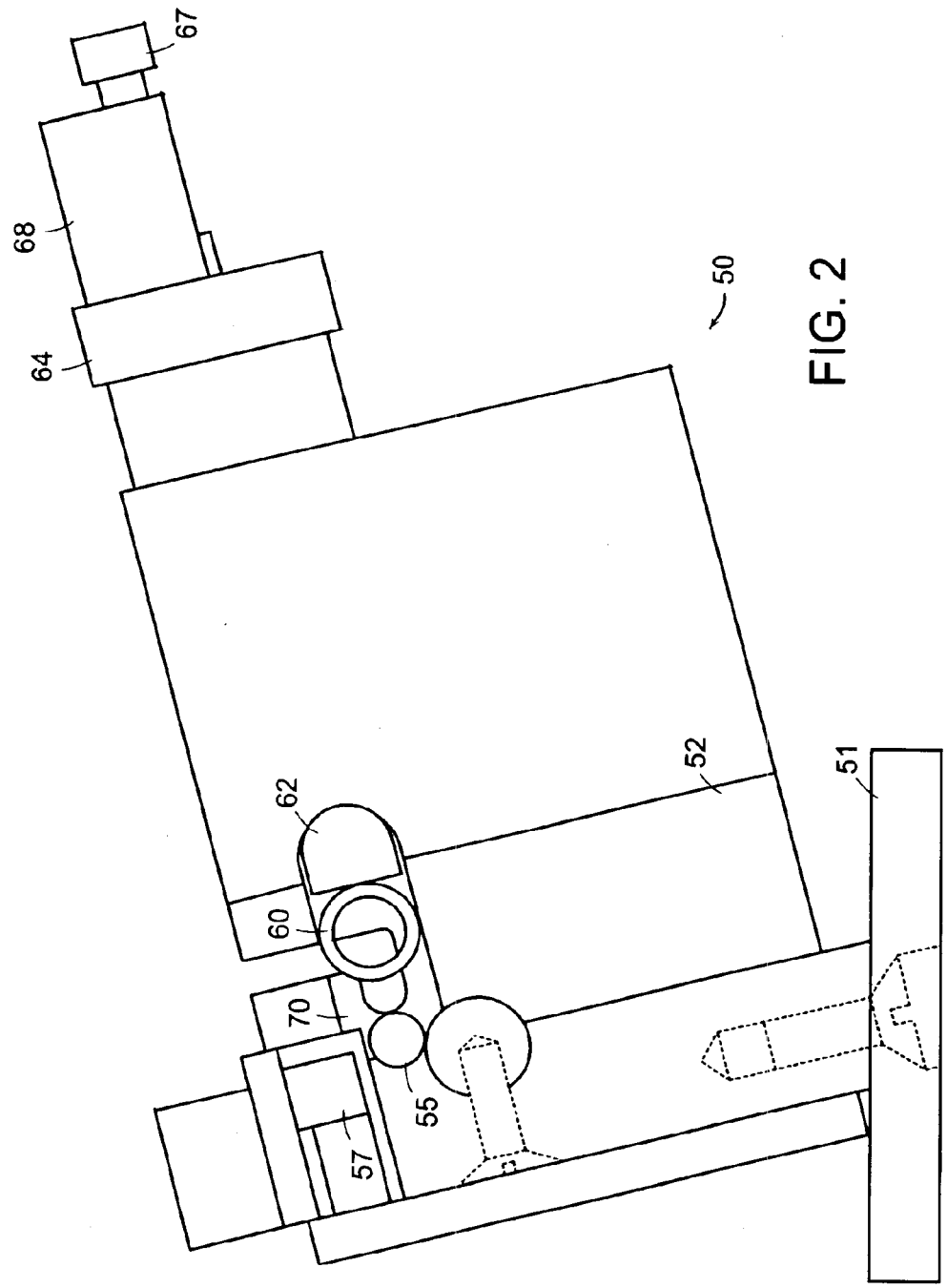
FIG. 2 shows a side cross-sectional view of the rolling apparatus of the invention.
Figure 3:
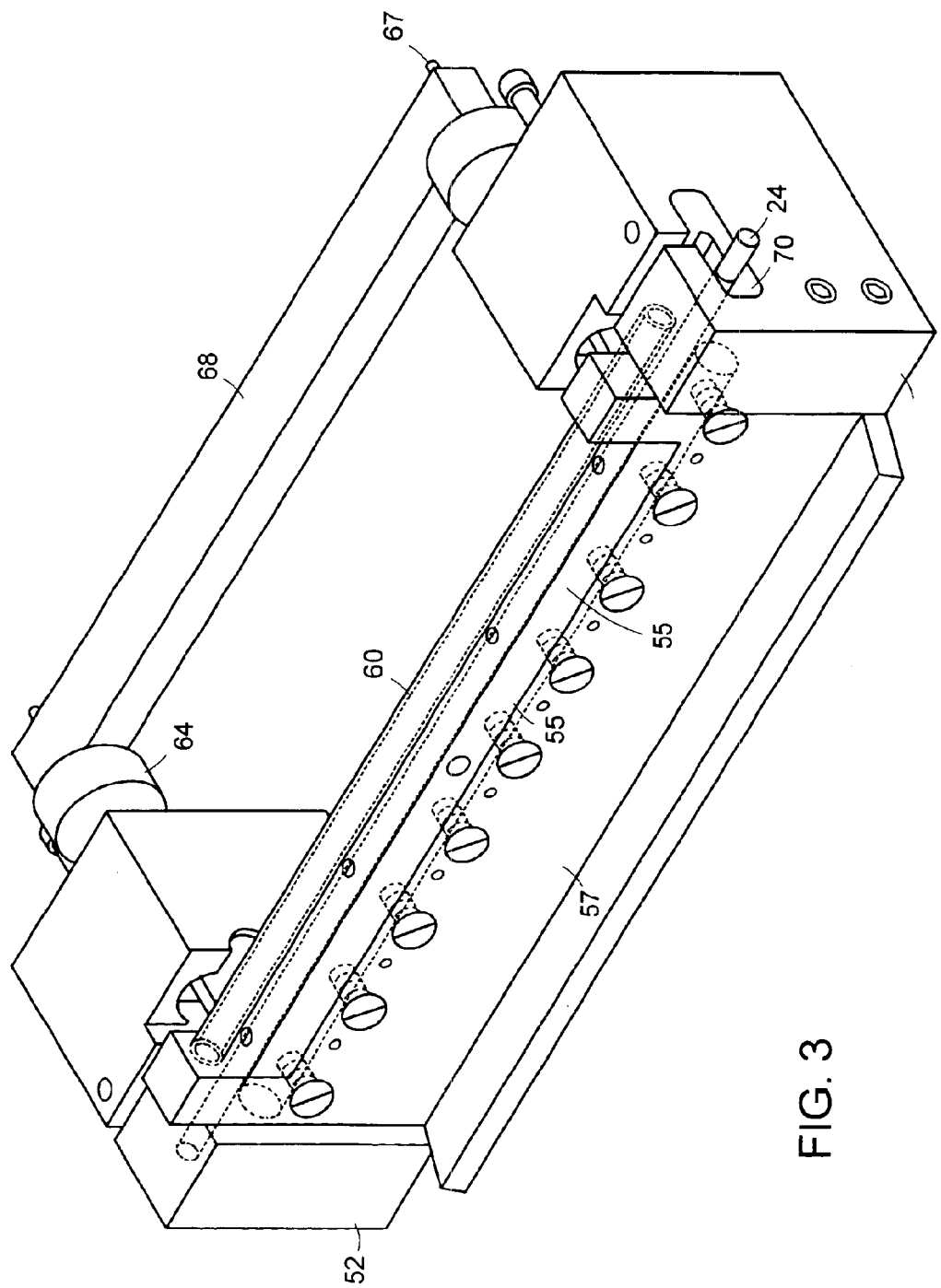
FIG. 3 shows a three-dimensional view of the rolling apparatus of the invention.

The second aspect of the system of the invention is a device for forming a tube from flagged ICL. Referring to FIG. 2, shown is the rolling device of the invention. The rolling device 50 comprises a stand 51 that supports two opposing mounts 52. Passing between and held in parallel arrangement by the opposing mounts are a porous tubular ceramic rod 55, a hollow chuck 57, and a spring-loaded roller 60. The ceramic rod 55 has a lumen running its length with one end of the ceramic rod is closed and the other end extending beyond the mount and open to serve as a port. Pores communicate between the lumen of the rod through to the surface for water to uniformly pass through. Above the level of the ceramic rod a hollow chuck 57 with machined holes that communicate between the interior and exterior of the chuck. The hollow chuck has a plurality of holes on the face towards the roller 60 and a port at one end for the attachment of a vacuum source. The spring-loaded roller 60 runs along the length of the ceramic rod creating a line of contact between the roller 60 and the ICL on mandrel 24. In each mount, the spring-loaded roller 60 is contacted by an end of a perpendicular rod 62 loaded by a coil spring contained in the mount. The perpendicular rod 62 passes through the mount via an extender rod 67. The perpendicular rods 62 can be disengaged from the roller 60 by engaging a solid bar 68 between the ends of the extender rods 67 and the spring housings 64. In each of the opposing mounts is a guide member 70 having an L-shaped groove where the top of the guide is open to accommodate one end of the mandrel and the bottom of the guide aligns the mandrel to engage it against the ceramic rod. When the spring-loaded roller is disengaged, the guides are open for the insertion of a mandrel between the opposing mounts. When the guides are loaded with a mandrel and the spring-loaded roller is engaged, the roller presses against the mandrel on one side such that the mandrel contacts the ceramic rod on the opposite side.

Before loading the guide with a mandrel, the vacuum and water sources are activated so that air is pulled through the machined holes in the hollow chuck to the interior of the chuck and the water is slowly passing from the lumen of the ceramic tube to its surface. The ends of the mandrel with the flagged ICL are placed in the guides with the free end of the flagged ICL upright and away from the rolling device. The spring-loaded roller is actuated against the mandrel forcing the mandrel to contact the porous ceramic rod. The mandrel is then rotated to wrap the ICL around the mandrel. The ICL is held taught by the vacuum from the hollow chuck 57. As the mandrel is rotated, successive portions of the ICL contact the porous ceramic rod and are lightly moistened by the water flowing out of the ceramic rod. The mandrel is rotated until the entire piece of ICL is wrapped around the mandrel.

The bioengineered constructs produced by the devices and methods of the invention are tubular in shape and may be formed to any length or thickness. The length of the construct is limited only by the size of the devices of the system and the length of the mandrel and the longest dimension of a sheet of material. The thickness of the construct may be chosen so that the final construct is one or more layers, depending on the number of times the mandrel that holds the sheet of material is rotated, with the limitation being the maximum thickness that the apparatus can manage. For a single layer construct, there will be some overlap where a bonding region is formed to maintain the tubular shape of the final construct. The diameter of the tube is determined by the diameter of the mandrel chosen.

To form a tubular construct, a mandrel is chosen with a diameter measurement that will determine the final inner diameter of the formed tube construct. The mandrel is preferably cylindrical or oval in cross section and made of glass, stainless steel, ceramic, or plastic and preferably of a nonreactive, medical grade composition. The number of layers intended for the tubular construct to be formed corresponds with the number of times an ICL is wrapped around a mandrel and over itself. The number of times the ICL can be wrapped depends on the width of the processed ICL sheet. For a two layer tubular construct, the width of the sheet must be sufficient for wrapping the sheet around the mandrel at least twice. Similarly, the length of the mandrel will dictate the length of the tube that can be formed on it. For ease in handling the construct on the mandrel, the mandrel should be longer than the length of the construct so the mandrel, and not the construct being formed, is contacted when handled.

It is preferred that the mandrel is provided with an elastic sleeve. The sleeve may be a nonreactive, medical grade quality, elastomeric material. While a tubular ICL construct may be formed directly on the mandrel surface, the sleeve facilitates the removal of the formed tube from the mandrel and does not adhere to, react with, or leave residues on the ICL. To remove the formed construct, the sleeve may be pulled off from one end of the mandrel and carry the construct from the mandrel with it. Because the processed ICL only lightly adheres to the sleeve and is more adherent to other ICL layers, fabricating ICL tubes is facilitated as the tubulated construct may be removed from the mandrel without stretching or risking damage to the tube construct. In the most preferred embodiment, the elastic sleeve comprises KRATON® (Shell Chemical Company), a thermoplastic rubber composed of styrene-ethylene/butylene-styrene copolymers with a very stable saturated midblock.

For illustration, a two-layer tubular construct with a 4 mm inner diameter and an additional 20% overlap is formed on a mandrel having about a 4 mm diameter. The mandrel is provided with a KRATON® sleeve approximately as long as the length of the mandrel and longer than the construct to be formed on it. A sheet of ICL is trimmed so that the width dimension is about 28 mm and the length dimension may vary depending on the desired length of the construct. In the sterile field of a laminar flow cabinet, the ICL is then formed into an ICL collagen tube by the following process. The ICL is moistened along one edge and is aligned with the sleeve-covered mandrel and, leveraging the adhesive nature of the ICL, it is "flagged" along the length of the sleeve-covered mandrel and dried in position for at least 10 minutes. The flagged ICL is then hydrated and wrapped around the mandrel and then over itself one full revolution plus 20% of the circumference, for a 120% total overlap, to serve as a bonding region and to provide a tight seam. To obtain a tubular construct with the mucosal side of the ICL as the lumen of the formed construct, the mucosal side of the ICL is moistened along one edge, flagged on the mandrel, and wrapped so that the mucosal side of the ICL faces the mandrel. Using the method above, a tubular construct can be made with the mucosal side of the ICL as the lumen or, alternatively, the serosal side of the ICL as the lumen by orienting the ICL appropriately during flagging.

For the formation of single layer tubular construct, the ICL must be able to wrap around the mandrel one full revolution and at least about a 5% additional revolution as an overlap to provide a bonding region that is equal to about 5% of the circumference of the construct. For a two-layer construct, the ICL must be able to wrap around the mandrel at least twice and preferably an additional 5% to 20% revolution as an overlap. While the two-layer wrap provides a bonding region of 100% between the ICL surfaces, the additional percentage for overlap ensures a minimum of 2 layers throughout the graft. For a three-layer construct, the ICL must be able to wrap around the mandrel at least three times and preferably an additional 5% to 20% revolution as an overlap. The construct may be prepared with any number of layers depending on the specifications for a graft required by the intended indication. Typically, a tubular construct will have 10 layers or less, preferably between 2 to 6 layers and more preferably 2 or 3 layers with varying degrees of overlap. During and after wrapping, any air bubbles, folds, and creases are smoothed out from under the material and between the layers.

The layers of the wrapped ICL are then bonded together by dehydrating them while in wrapped arrangement on the sleeve-covered mandrel. While not wishing to be bound by theory, dehydration brings the extracellular matrix components, such as collagen fibers, in the layers together when water is removed from the spaces between the fibers in the matrix. Dehydration may be performed in air, in a vacuum, or by chemical means such as by acetone or an alcohol such as ethyl alcohol or isopropyl alcohol. Dehydration may be done to room humidity, normally between about 10% RH to about 50% RH. Dehydration may be performed by placing the mandrel with the ICL layers into the oncoming airflow of a laminar flow cabinet for at least about 1 hour up to 24 hours at ambient room temperature, approximately 20° C., and at room humidity. At this point the wrapped dehydrated ICL constructs may be then pulled off the mandrel via the sleeve or left on for further processing. The constructs may be rehydrated in an aqueous solution, preferably water, by transferring them to a room temperature container containing rehydration agent for at least about 10 to about 15 minutes to rehydrate the layers without separating or delaminating them. The thus formed collagen tube construct is then used to form a prosthesis, preferably a bioremodelable prosthesis.

The constructs are then preferably crosslinked together by contacting them with a crosslinking agent, preferably a chemical crosslinking agent that preserves the bioremodelability of the ICL material. As mentioned above, the dehydration brings the extracellular matrix components of adjacent ICL layers together for crosslinking those layers of the wrap together to form chemical bonds between the components and thus bond the layers together. Alternatively, the constructs may be rehydrated before crosslinking by contacting an aqueous solution, preferably water, by transferring them to a room temperature container containing rehydration agent for at least about 10 to about 15 minutes to rehydrate the layers without separating or delaminating them. Crosslinking the bonded prosthetic device also provides strength and durability to the device to improve handling properties. Various types of crosslinking agents are known in the art and can be used such as ribose and other sugars, oxidative agents and aldehydes. A preferred crosslinking agent is 1-ethyl-3-(3-dimethylaminopropyl) carbodiimide hydrochloride (EDC). In an another preferred method, sulfo-N-hydroxysuccinimide is added to the EDC crosslinking agent as described by Staros, J. V., Biochem, 21, 3950–3955, 1982. Besides chemical crosslinking agents, the layers may be bonded together by physical means such as dehydrothermal (DHT) and ultraviolet (UV) methods or by other methods such as with fibrin-based glues or medical grade adhesives including cyanoacrylate, polyurethane, vinyl acetate or polyepoxy. In the most preferred method, EDC is solubilized in water at a concentration preferably between about 0.01 mM to about 100 mM, more preferably between about 0.1 mM to about 10 mM, most preferably at about 1.0 mM. Besides water, phosphate buffered saline or (2-[N-morpholino]ethanesulfonic acid) (MES) buffer may be used to dissolve the EDC. In addition, other agents may be added to the solution such as acetone or an alcohol may be added up to 99% v/v in water to modulate the crosslinking. EDC crosslinking solution is prepared immediately before use as EDC will lose its activity over time. To contact the crosslinking agent to the ICL, the hydrated, ICL tubular constructs are transferred to a container such as a shallow pan and the crosslinking agent gently decanted to the pan ensuring that the ICL layers are both covered and free-floating and that no air bubbles are present under or within the layers of ICL constructs. The pan is covered and the layers of ICL are treated with crosslinking agent for between about 4 to about 24 hours after which time the crosslinking solution is decanted and disposed of.

Constructs are rinsed in the pan by contacting them with a rinse agent to remove residual crosslinking agent. A preferred rinse agent is water or other aqueous solution. Preferably, sufficient rinsing is achieved by contacting the chemically bonded constructs three times with equal volumes of sterile water for about five minutes for each rinse. If the constructs have not been removed from the mandrels, they may be removed at this point by pulling the sleeves from the mandrels. The constructs are then allowed to dry and when dry, the sleeve may be removed from the lumen of the constructs simply by pulling it out by one of the free ends.

In embodiments where the construct will be used as a vascular graft, the luminal surface of the construct may be rendered less thrombogenic by applying a deposited collagen layer or heparin, or both, to the lumen of the formed tube. Heparin can be applied to the prosthesis by a variety of well-known techniques. For illustration, heparin can be applied to the prosthesis in the following three ways. First, benzalkonium heparin (BA-Hep) isopropyl alcohol solution is applied to the prosthesis by vertically filling the lumen or dipping the prosthesis in the solution and then air-drying it. This procedure treats the collagen with an ionically bound BA-Hep complex. Second, EDC can be used to activate the heparin and then to covalently bond the heparin to the collagen fiber. Third, EDC can be used to activate the collagen, then covalently bond protamine to the collagen and then ionically bond heparin to the protamine. Many other coating, bonding, and attachment procedures are well known in the art that could also be used.

The following examples are provided to better elucidate the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

Method for Making an ICL Tube Construct

In the sterile field of a laminar flow cabinet, the ICL was formed into ICL collagen tubes by the following process. Lymphatic tags were trimmed from the serosal surface of the ICL. The ICL was blotted with sterile absorbent towelettes to absorb excess water from the material and then spread on a porous polycarbonate sheet and dried in the oncoming airflow of the laminar flow cabinet. Once dry, ICL was cut into 28.5 mm×10 cm pieces for a 2 layer graft with approximately a 20% overlap. To support the ICL in the formation of the tubes, a cylindrical stainless steel mandrel with a diameter of about 4 mm was covered with KRATON®, an elastic sleeve material that facilitates the removal of the formed collagen tube from the mandrel and does not adhere or react with the ICL.

The flagging apparatus of the invention was used to contact and adhere the edge of a sheet of ICL to a mandrel. The long edge of the ICL was moistened with sterile water on the sleeve around the mandrel and adhered to the mandrel and allowed to dry for about 15 minutes to form a "flag".

The rolling machine of the invention was used to roll a flagged sheet of ICL around the mandrel to form a tube of ICL. The ICL was rolled around the mandrel and over itself one complete revolution. After rolling was complete, air bubbles, folds, and creases were smoothed out from under the material and between the layers. The mandrels and rolled constructs were allowed to sit in the oncoming airflow of the laminar flow cabinet and allowed to dry for about an hour in the cabinet at room temperature, approximately 20° C.

Chemical crosslinking solution of either crosslinked 1 mM EDC or 10 mM EDC/25% acetone v/v in water, in volumes of about 50 mL crosslinking solution per tube, was prepared immediately before crosslinking. The hydrated ICL tubes were then transferred to either of two cylindrical vessels containing either crosslinking agent. The vessel was covered and allowed to sit for about 18±2 hours in a fume hood, after which time the crosslinking solution was decanted and disposed. ICL tubes were then rinsed three times with sterile water for about 5 minutes per rinse.

The crosslinked ICL tubes were then removed from the mandrel by pulling the Kraton sleeve off the mandrel from one end. Once removed, the ICL tubes containing the Kraton were allowed to dry for an hour in a laminar air flow hood. Once dried, the sleeve was removed from the lumen of each ICL tube by pulling it out from one end.

ICL tubes were sterilized in 0.1% peracetic acid at approximately pH 7.0 overnight according to the methods described in commonly owned U.S. Pat. No. 5,460,962, the disclosure of which is incorporated herein in its entirety. The ICL tubes were then rinsed of sterilization solution three times with sterile water for about 5 minutes per rinse. The peracetic acid sterilized ICL collagen tubes were then dried in a laminar flow hood and then packaged in sterile 15 mL conical tubes until implantation.

Although the foregoing invention has been described in some detail by way of illustration and example for purposes of clarity and understanding, it will be obvious to one of skill in the art that certain changes and modifications may be practiced within the scope of the appended claims.

We claim:

1. An apparatus for forming a tube construct from a planar sheet matrix, comprising:

a stand supporting two opposing mounts and spanning between the opposing mounts are a mandrel, a porous rod, and a spring-loaded roller held in parallel arrangement;

a guide for aligning and engaging the mandrel on the opposing mounts; and, a means for imparting a tangential force on the planar sheet matrix to prevent wrinkling;

wherein the porous rod has a lumen running its length and has pores that communicate between the lumen of the porous rod through to the surface of the rod for water to uniformly pass through;

wherein the spring-loaded roller runs along the length of the porous rod creating a line of contact between the roller and the mandrel; and, wherein the mandrel is contacted with a planar sheet of matrix and is rotated such that successive portions of the matrix contact the porous rod and become lightly moistened by the water passing through the pores of the porous rod and become wrapped around the mandrel to form a tube construct.

2. The apparatus of claim 1, further comprising:

a hollow chuck above the level of the ceramic rod, the hollow chuck having machined holes that communicate between the interior and exterior of the hollow chuck.

3. The apparatus of claim 2, wherein:

the hollow chuck has a plurality of holes on the face towards the spring-loaded roller; and the hollow chuck has a port at one end for the attachment of a vacuum source.

4. The apparatus of claim 1, further comprising:

a perpendicular rod wherein, in each mount, the spring-loaded roller is contacted by an end of the perpendicular rod loaded by a coil spring contained in the mount.

5. The apparatus of claim 4, further comprising:

first and second extender rods;

a solid bar; and first and second spring housings; wherein the perpendicular rod passes through each mount via the extender rod and the perpendicular rod can be disengaged from the spring-loaded roller by engaging the solid bar between the ends of the first and second extender rods and the first and second spring housings.

6. The apparatus of claim 3, further comprising:

a guide member in each of the opposing mounts, the guide member having an L-shaped groove such that the top of the guide member is open to accommodate one end of the mandrel and the bottom of the guide member aligns the mandrel to engage the mandrel against the porous rod.

7. The apparatus of claim 6, wherein:

when the spring-loaded roller is disengaged, the guide members are open for the insertion of the mandrel between the opposing mounts; and when the guide members are loaded with the mandrel and the spring-loaded roller is engaged, the roller presses against the mandrel on one side such that the mandrel contacts the ceramic rod on the opposite side.

8. The apparatus of claim 6, further comprising:

a vacuum source; and a water source; wherein, before the guide members are loaded with the mandrel, the vacuum and water sources are activated so that air is pulled through the holes in the hollow chuck to the interior of the hollow chuck and water is passed from the lumen of the porous tube to its surface.

* * * * *